United States Patent
Koshiol et al.

(10) Patent No.: US 7,471,980 B2
(45) Date of Patent: Dec. 30, 2008

(54) SYNCHRONIZING CONTINUOUS SIGNALS AND DISCRETE EVENTS FOR AN IMPLANTABLE MEDICAL DEVICE

(75) Inventors: Allan T. Koshiol, Lino Lakes, MN (US); LeAnne Eberle, St. Louis Park, MN (US); Hiten J. Doshi, Plymouth, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 70 days.

(21) Appl. No.: 10/743,567

(22) Filed: Dec. 22, 2003

(65) Prior Publication Data

US 2005/0137627 A1   Jun. 23, 2005

(51) Int. Cl.
    *A61N 1/362* (2006.01)
(52) U.S. Cl. ......................................................... 607/9
(58) Field of Classification Search .................. 607/5, 607/9
    See application file for complete search history.

(56) References Cited

U.S. PATENT DOCUMENTS

| | | | |
|---|---|---|---|
| 4,223,678 A | 9/1980 | Langer et al. |
| 4,316,249 A | 2/1982 | Gallant et al. |
| 4,407,288 A | 10/1983 | Langer et al. |
| 4,527,567 A | 7/1985 | Fischler et al. |
| 4,531,527 A | 7/1985 | Reinhold, Jr. et al. |
| 4,549,552 A | 10/1985 | Groch et al. |
| 4,596,255 A | 6/1986 | Snell et al. |
| 4,601,291 A | 7/1986 | Boute et al. |
| 4,791,936 A | 12/1988 | Snell et al. |
| 4,809,697 A | 3/1989 | Causey, III et al. |
| 4,825,869 A | 5/1989 | Sasmor et al. |
| 4,944,298 A | 7/1990 | Sholder |
| 4,964,410 A | 10/1990 | Leahey et al. |
| 4,979,506 A | 12/1990 | Silvian |
| 5,209,228 A | 5/1993 | Cano et al. |

(Continued)

FOREIGN PATENT DOCUMENTS

EP    0565084 A2    10/1993

(Continued)

OTHER PUBLICATIONS

"International Search Report for corresponding PCT Application No. PCT/US2004/042269", (Mar. 31, 2005), 5 pgs.

(Continued)

*Primary Examiner*—Angela D. Sykes
*Assistant Examiner*—Rex Holmes
(74) *Attorney, Agent, or Firm*—Schwegman, Lundberg & Woessner, P.A.

(57) ABSTRACT

A system comprises an implantable medical device (IMD). The IMD includes at least one electrical input to receive sensed electrical activity of a heart and a sampler circuit coupled to the at least one electrical input. The sampler circuit generates sampled values of the sensed electrical activity. The IMD includes a clock circuit that generates readable values representative of absolute time. The IMD also includes a controller circuit coupled to the sampler circuit and the clock circuit. The controller circuit processes the sampled values and generate at least one marker to indicate a detected event related to the electrical activity. The controller circuit also stores a timestamp of absolute time of the detected event with the at least one marker in memory.

32 Claims, 7 Drawing Sheets

U.S. PATENT DOCUMENTS

| | | | |
|---|---|---|---|
| 5,217,021 A | 6/1993 | Steinhaus et al. | |
| 5,311,874 A | 5/1994 | Baumann et al. | |
| 5,312,446 A * | 5/1994 | Holschbach et al. | 607/9 |
| 5,357,969 A | 10/1994 | Herleikson | |
| 5,391,188 A | 2/1995 | Nelson et al. | |
| 5,402,794 A | 4/1995 | Wahlstrand et al. | |
| 5,404,880 A | 4/1995 | Throne | |
| 5,413,594 A | 5/1995 | Williams | |
| 5,417,714 A | 5/1995 | Levine et al. | |
| 5,431,691 A * | 7/1995 | Snell et al. | 607/27 |
| 5,431,692 A | 7/1995 | Hansen et al. | |
| 5,476,485 A | 12/1995 | Weinberg et al. | |
| 5,487,755 A | 1/1996 | Snell et al. | |
| 5,507,786 A | 4/1996 | Morgan et al. | |
| 5,511,553 A | 4/1996 | Segalowitz | |
| 5,513,645 A | 5/1996 | Jacobson et al. | |
| 5,549,654 A | 8/1996 | Powell | |
| 5,578,063 A | 11/1996 | Bocek et al. | |
| 5,591,214 A | 1/1997 | Lu | |
| 5,603,331 A | 2/1997 | Heemels et al. | |
| 5,609,615 A | 3/1997 | Sanders et al. | |
| 5,628,776 A | 5/1997 | Paul et al. | |
| 5,653,737 A | 8/1997 | van Lake | |
| 5,683,431 A | 11/1997 | Wang | |
| 5,709,712 A | 1/1998 | Paul et al. | |
| 5,722,999 A | 3/1998 | Snell | |
| 5,732,708 A | 3/1998 | Nau et al. | |
| 5,759,196 A | 6/1998 | Hess et al. | |
| 5,782,890 A | 7/1998 | Wahlstrand et al. | |
| 5,792,207 A | 8/1998 | Dietrich | |
| 5,814,083 A | 9/1998 | Hess et al. | |
| 5,891,178 A | 4/1999 | Mann et al. | |
| 5,904,708 A * | 5/1999 | Goedeke | 607/18 |
| 5,908,392 A * | 6/1999 | Wilson et al. | 600/509 |
| 5,925,067 A | 7/1999 | Lu | |
| 5,974,341 A | 10/1999 | Er et al. | |
| 5,978,707 A | 11/1999 | Krig et al. | |
| 6,016,442 A | 1/2000 | Hsu et al. | |
| 6,016,446 A | 1/2000 | Belalcazar | |
| 6,045,513 A | 4/2000 | Stone et al. | |
| 6,067,471 A | 5/2000 | Warren | |
| 6,076,015 A | 6/2000 | Hartley et al. | |
| 6,091,990 A | 7/2000 | Hsu et al. | |
| 6,108,577 A | 8/2000 | Benser | |
| 6,112,117 A | 8/2000 | KenKnight et al. | |
| 6,161,043 A * | 12/2000 | McClure et al. | 607/27 |
| 6,243,606 B1 | 6/2001 | Mann et al. | |
| 6,263,244 B1 | 7/2001 | Mann et al. | |
| 6,308,095 B1 | 10/2001 | Hsu et al. | |
| 6,311,089 B1 | 10/2001 | Mann et al. | |
| 6,312,378 B1 | 11/2001 | Bardy | |
| 6,400,985 B1 * | 6/2002 | Amely-Velez | 607/9 |
| 6,427,083 B1 * | 7/2002 | Owen et al. | 607/5 |
| 6,442,428 B1 * | 8/2002 | Shankar et al. | 607/9 |
| 6,449,504 B1 | 9/2002 | Conley et al. | |
| 6,459,929 B1 | 10/2002 | Hopper et al. | |
| 6,459,934 B1 | 10/2002 | Kadhiresan | |
| 6,535,763 B1 | 3/2003 | Hiebert et al. | |
| 6,625,488 B2 * | 9/2003 | Poore et al. | 607/9 |
| 6,636,765 B2 * | 10/2003 | Amely-Velez | 607/9 |
| 2002/0065540 A1 * | 5/2002 | Lebel et al. | 607/60 |
| 2002/0077859 A1 | 6/2002 | Stahmann et al. | |
| 2002/0082509 A1 | 6/2002 | Vanderlinde et al. | |
| 2002/0107550 A1 * | 8/2002 | Amely-Velez | 607/9 |
| 2002/0151809 A1 | 10/2002 | Conley et al. | |

FOREIGN PATENT DOCUMENTS

| | | |
|---|---|---|
| EP | 0711531 A1 | 5/1996 |
| EP | 0850661 A1 | 7/1998 |
| EP | 1245248 A2 | 10/2002 |

OTHER PUBLICATIONS

Tanenbaum, A. S., "Computer Networks", *Prentice-Hall, Inc., Englewood Cliffs, NJ,* (1981), 125-128.

"U.S. Appl. No. 09/382,154, filed Aug. 22, 1999, Prosecution File History", (now US 6,535,763),30 pgs.

"U.S. Appl. No. 10/353,113, filed Jan. 27, 2003, Prosecution File History", (now US 7,117,037),38 pgs.

"U.S. Appl. No. 10/680,731, filed Oct. 7, 2003, Prosecution File History", 48 pgs.

* cited by examiner

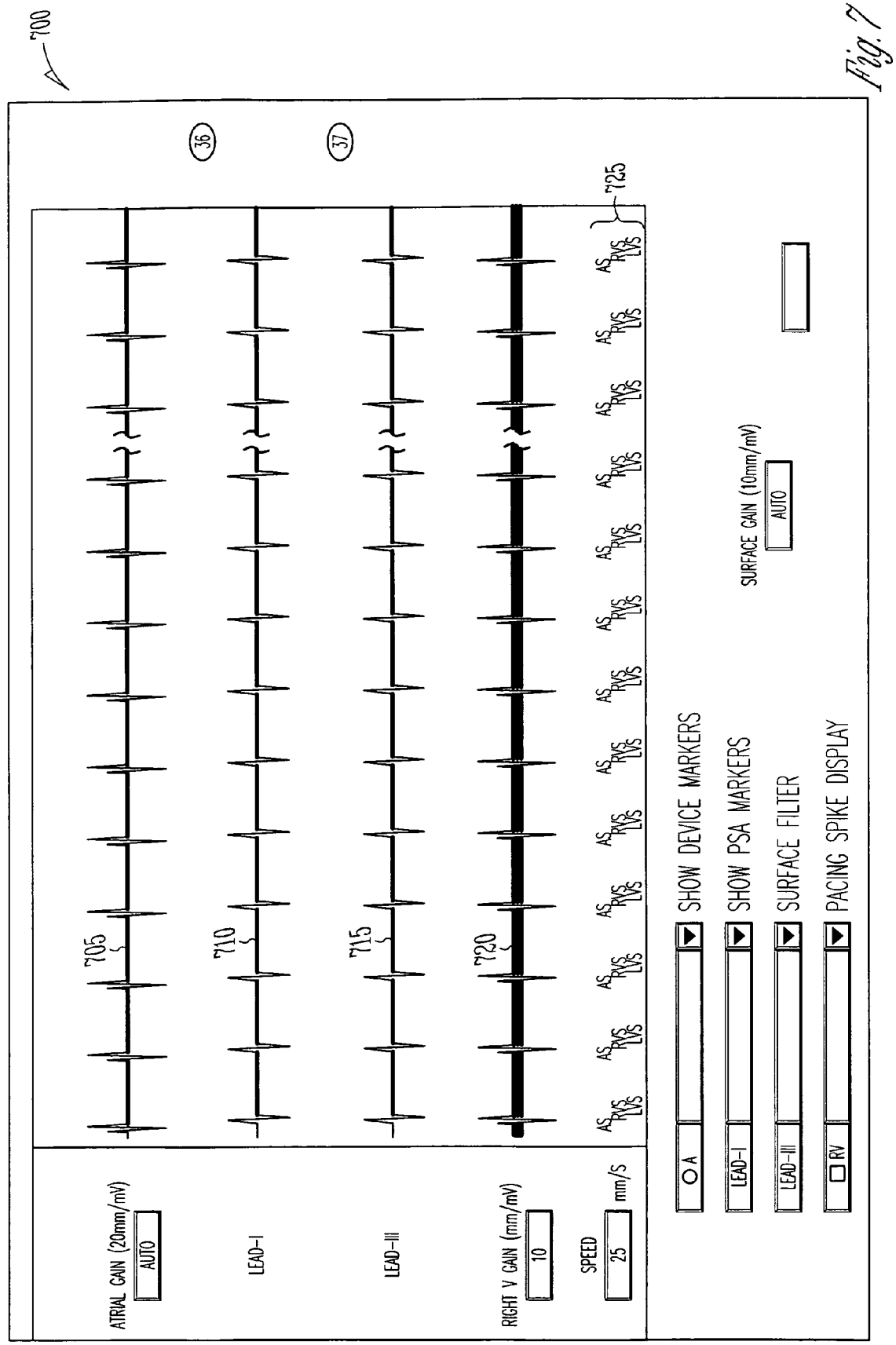

SYNCHRONIZING CONTINUOUS SIGNALS AND DISCRETE EVENTS FOR AN IMPLANTABLE MEDICAL DEVICE

CROSS REFERENCE TO RELATED APPLICATIONS

This patent application is related to U.S. Pat. No. 6,535,763 to Heibert et al., entitled "EVENT MARKER ALIGNMENT BY INCLUSION OF EVENT MARKER TRANSMISSION LATENCY IN THE REAL-TIME DATA STREAM," and U.S. patent application Ser. No. 10/680,731 to Lent et al., entitled METHOD AND APPARATUS FOR MANAGING DATA FROM MULTIPLE SENSING CHANNELS," each of which are assigned to Cardiac Pacemakers, Inc., and each of which are incorporated herein by reference.

TECHNICAL FIELD

This patent application relates generally to devices that communicate with implantable medical devices and, in particular, but not by way of limitation, to a system and method for synchronizing continuous signals and discrete events.

BACKGROUND

Implantable medical devices (IMDs) are devices designed to be implanted into a patient. Some examples of these devices include cardiac rhythm management devices such as implantable pacemakers and implantable cardioverter defibrillators (ICDs). The devices are used to treat patients using electrical therapy and to aid a physician or caregiver in patient diagnosis through internal monitoring of a patient's condition. The devices may include electrical leads in communication with sense amplifiers to monitor electrical heart activity within a patient, and often include sensors to monitor other internal patient parameters. In general, the sensors convert sensed internal parameters into electrical signals. The electrical signals monitored within the patient and the electrical signals from the sensors can be quantized by analog-to-digital converters and stored in the IMD as data.

Implantable medical devices are able to communicate with external devices using wireless communication methods. The external devices are often external programmers that use wireless communication links to change performance parameters in the implantable device. The implantable device also wirelessly transmits the stored data to an external device. The external device may then display the collected data on a computer screen display or a strip chart recorder.

The IMDs are also able to detect events, such as by monitoring the electrical heart activity signals. In a cardiac rhythm management device, these events can include heart chamber expansions and contractions. The IMD identifies such a detected event by generating a marker for transmission to the external device. This marker is usually in the form of a binary code. Transmitting such a binary code allows the external device to label an event on the screen display or strip chart recorder.

As technology used in implantable medical devices advances, the devices will be able to collect data from multiple leads and multiple sensors from multiple locations. They also will detect events occurring from such multiple sources. Potentially, this results in a large amount of data to be collected by the implantable device and transmitted to the external device. Additionally, the data may be collected from different types of sensors at different times and/or sampling rates, or processing may be done on the collected data by the implantable device before the data is transmitted to an external device. Thus, the relative timing between the events and the data as displayed at the external device is often different from the relative timing of the events and data as they actually occur.

The large amount of data coming from various sources complicates the task of reconstructing the information for a display while preserving the correct timing relationship among the data and markers. What is needed is an improved method of managing data that is available from implantable medical devices.

SUMMARY

This document discusses, among other things, systems and methods involving alignment of detected event markers within a stream of transmitted data that is either transmitted in substantially real time or transmitted after it has been previously stored.

In one example, a system comprises an implantable medical device (IMD). The IMD includes at least one electrical input to receive sensed electrical activity of a heart, a sampler circuit coupled to the at least one electrical input that is operable to generate sampled values of the sensed electrical activity and a clock circuit that is operable to generate readable values representative of time. The IMD also includes a controller circuit coupled to the sampler circuit and the clock circuit. The controller circuit is operable to process the sampled values and generate at least one marker to indicate a detected event related to the electrical activity. The controller circuit is also operable to read a clock circuit value as a timestamp of absolute time of when the detected event occurred, and store the at least one marker with the timestamp in memory.

In another example, this document discusses a method that comprises sensing electrical activity of a heart using an implantable device, detecting events associated with the electrical activity, storing the detected events in a memory as event markers where the markers include a timestamp of an absolute time when the events occurred, and transmitting the event markers to an external device. Other examples and advantages are also discussed in the following detailed description and represented in the drawings that form a part thereof.

BRIEF DESCRIPTION OF THE DRAWINGS

FIG. 7 is an illustration of one embodiment of a screen display of an external device.

DETAILED DESCRIPTION

In the following detailed description, reference is made to the accompanying drawings which form a part hereof, and specific embodiments in which the invention may be practiced are shown by way of illustration. It is to be understood that other embodiments may be used and structural changes may be made without departing from the scope of the present invention.

The present application discusses, among other things, systems and methods involving alignment, within a stream of transmitted data, of event markers representing detected events. Such data is either transmitted in real time as it is being acquired or, alternatively, is transmitted after it has been previously been acquired and stored.

Figure 1:
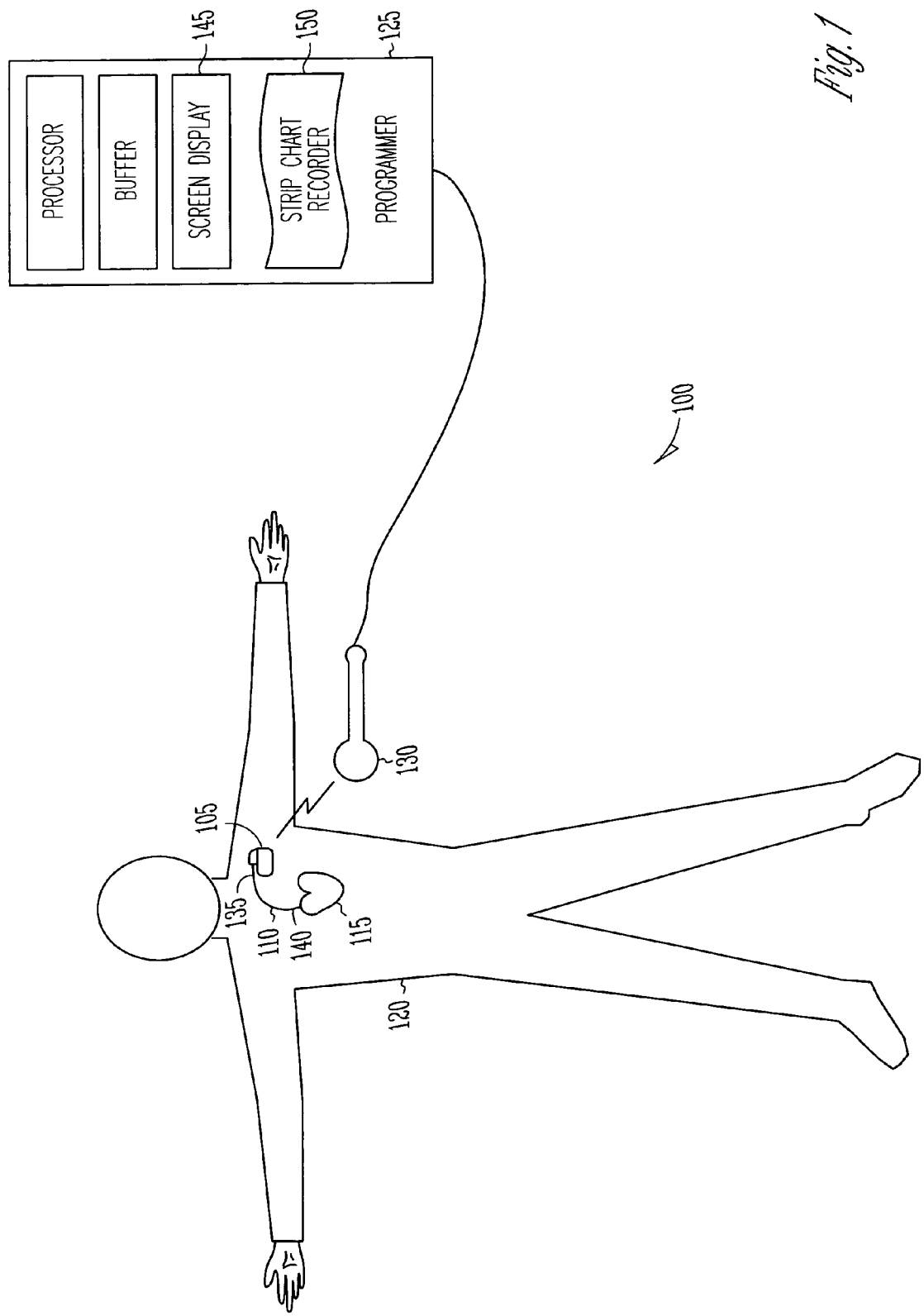
FIG. 1 is an illustration of a system that uses an implantable medical device.

FIG. 1 illustrates an embodiment of a system 100 that uses an implantable medical device (IMD) 105. The system 100 shown is one embodiment of portions of a system 100 used to treat a cardiac arrhythmia. A pulse generator (PG) or other implantable medical device (IMD) 105 coupled by a cardiac lead 110, or additional leads, to a heart 115 of a patient 120. Examples of IMD 105 include, without limitation, a pacer, a defibrillator, a cardiac resynchronization therapy (CRT) device, or a combination of such devices. The present subject matter relates to any IMD that can transmit data while implanted in a patient 120. Cardiac lead 110 includes a proximal end 135 that is coupled to IMD 105 and a distal end 140, coupled to one or more portions of a heart 115. System 100 also includes a programmer or other external device 125 that provides wireless communication with the IMD 105, such as by using a telemetry device 130. In one example, the external device 125 is able to communicate one or more operational parameters to the implantable device 105 in order to program the IMD 105.

Figure 2:
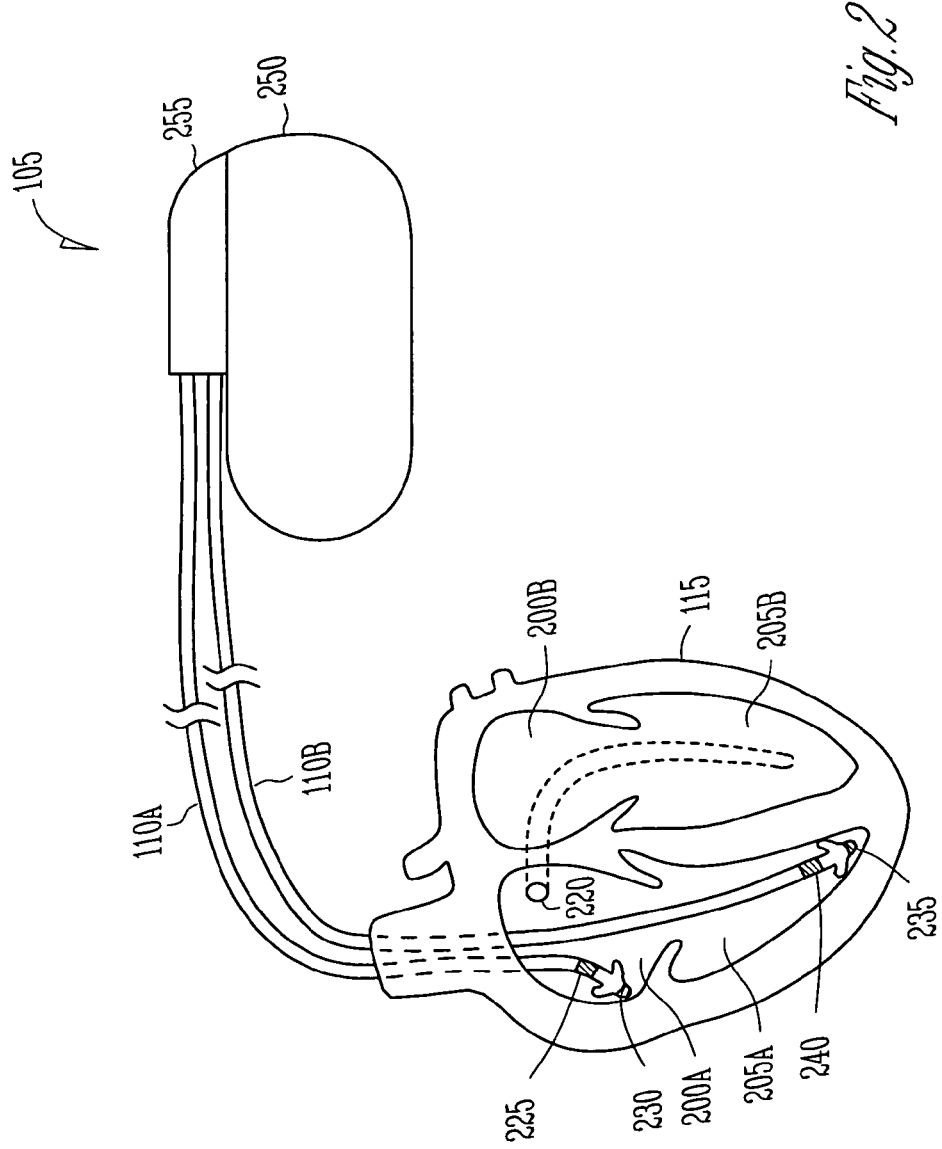
FIG. 2 is an embodiment of an implantable medical device coupled by leads to a heart.

FIG. 2 illustrates an IMD 105 coupled by one or more leads 110A-B to heart 115. Heart 115 includes a right atrium 200A, a left atrium 200B, a right ventricle 205A, a left ventricle 205B, and a coronary sinus 220 extending from right atrium 200A. In this embodiment, atrial lead 110A includes electrodes (electrical contacts, such as ring electrode 225 and tip electrode 230) disposed in, around, or near an atrium 200 of heart 115 for sensing signals and/or delivering pacing therapy to the atrium 200. Lead 110A optionally also includes additional electrodes, such as for delivering atrial and/or ventricular cardioversion/defibrillation and/or pacing or resynchronization therapy to heart 115.

Ventricular lead 110B includes one or more electrodes, such as tip electrode 235 and ring electrode 240, for delivering sensing signals and/or delivering pacing therapy. Lead 110B optionally also includes additional electrodes, such as for delivering atrial and/or ventricular cardioversion/defibrillation and/or pacing therapy to heart 115. IMD 105 includes components that are enclosed in a hermetically-sealed housing or "can" 250. Additional electrodes may be located on the can 250, or on an insulating header 255, or on other portions of IMD 105, for providing unipolar pacing and/or defibrillation energy in conjunction with the electrodes disposed on or around heart 115. Other forms of electrodes include meshes and patches which may be applied to portions of heart 115 or which may be implanted in other areas of the body to help "steer" electrical currents produced by IMD 105. In one embodiment, one of atrial lead 110A or ventricular lead 110B is omitted, i.e., a "single chamber" device is provided, rather than the dual chamber device illustrated in FIG. 2. In another embodiment, additional leads are provided for coupling the IMD 105 to other heart chambers and/or other locations in the same heart chamber as one or more of leads 110A-B. The present methods and systems will work in a variety of configurations and with a variety of electrical contacts or "electrodes."

Figure 3:
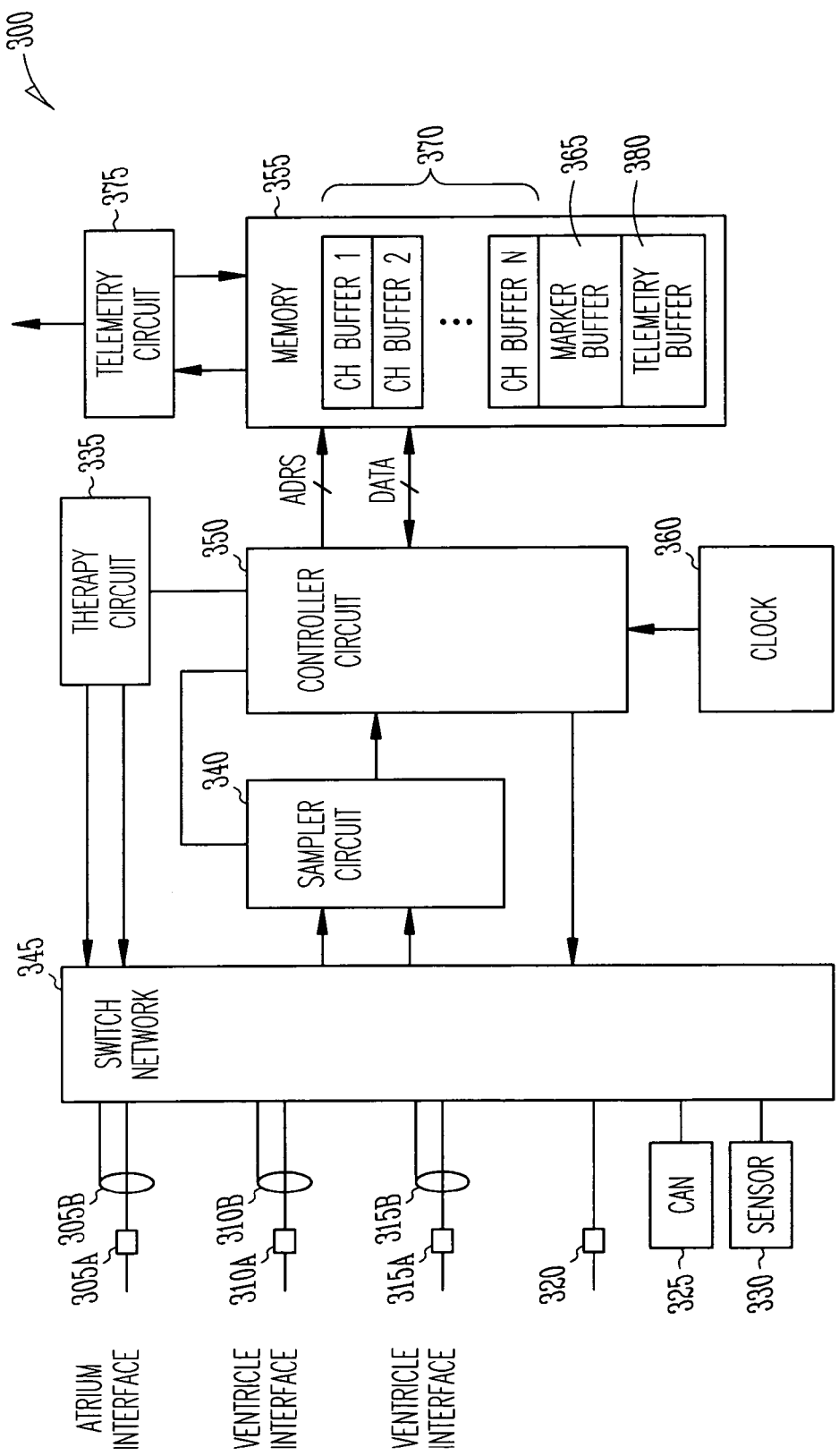
FIG. 3 shows another embodiment of an implantable medical device that is coupled to bipolar leads.

FIG. 3 shows an exemplary embodiment of an IMD 300 that is coupled to one or more leads, such as bipolar leads 305, 310, 315. The bipolar leads include tip electrodes 305A, 310A, 315A and ring electrodes 305B, 310B, 315B. The IMD 300 is also illustrated as coupled to unipolar lead that includes only a tip electrode 320. The IMD 300 includes a therapy circuit 335 to deliver electrical therapy to heart 115 through the leads and electrodes and a sampler circuit 340 to sample electrical signals sensed on the leads and electrodes. To sense the electrical signals, the IMD 300 includes sense amplifier circuits (such as in the sampler circuit 340 in FIG. 3) coupled to the switch network 345. The switching network 345 couples the therapy circuit 335 to the electrodes. It is also operable to couple the sampler circuit 340 to any combination of one or more electrodes.

Typically, the IMD 300 delivers therapy through the leads or senses voltages on the leads, such as between the tip electrodes 305A, 310A, 315A and ring electrodes 305B, 310B, 315B. The IMD 300 can also sense signals or deliver therapy between the unipolar lead electrode 320 and a can electrode 325. Sensing signals between a tip electrode 320 and a can electrode 325 is useful, for example, to obtain a sample of a signal during an evoked response. An evoked response is a heart contraction initiated by a pace pulse delivered by the IMD 300. In one example, the present system permits sensing between any two electrodes in the system. When the source of the sampling is a signal sensed between any two electrodes in the system, this source is sometimes referred to as a utility channel. In one example, the IMD 300 also includes one or more sensors 330 to generate electrical signals related to a physiologic parameter of a patient. In one embodiment the sensor is an accelerometer. In another embodiment, the sensor is an impedance sensor. In various embodiments the sensors are internal to the IMD 300 or implanted external to the IMD 300. The switching network 345 also provides for placing electrical signals derived from the sensor onto the sampler circuit 340.

The IMD 300 includes a controller circuit 350 that is operable to connect the therapy circuit 335 and sampler circuit 340 to the electrodes through the switch network 345. For example, controller circuit 350 is operable to switch tip electrode 305A and ring electrode 305B onto the inputs of the sampler circuit 340 through the switch network 345. The controller circuit 350 is also operable to place tip electrode 320 and can electrode 325 onto the inputs of sampler circuit 340 through the switch network 345. In one embodiment, the controller circuit is operable through logic circuits implemented in hardware. In another embodiment, controller circuit 340 includes a processor executing instructions contained in firmware. In yet another embodiment, the controller circuit 340 includes a processor executing software instructions. In yet another embodiment, the controller circuit includes combinations of hardware, software and firmware.

The sampler circuit 340 converts the sensed electrical signals from analog signals into digitized samples suitable for storage in a memory 355 within the IMD 300. In one embodiment, the sampling is performed using an analog-to-digital (A/D) converter. The sampler 340 can also be programmed using the controller 350 to change the rate at which data is collected. For example, in FIG. 2 cardiac lead 110B is shown placed in a right ventricle 205A of a heart 115. A sense amplifier attached to the lead generates signals suitable for sampling. The sampling creates an electrogram of the electrical activity in the ventricle 205A. In one embodiment, sampler circuit 340 is programmable to sample ventricular data at either 200 Hz or 400 Hz. The 400 Hz sampling creates an electrogram of the ventricular signals with increased fidelity over the 200 Hz sampling and generates data at twice the rate. Similarly, an electrogram of the atrium 200A is obtained using lead 10A. The sensor 330 also includes interface circuits such as filter circuits, amplifier circuits, impedance matching circuits, and the like, to generate signals appropriate for sampling by the sampler circuit 340. In one embodiment, the sensor is an accelerometer and data is sampled at 100 Hz. Other sampling rates are within contemplation of the present application.

Controller circuit 350 enables sampling of the signals and controls buffering or storage of the digitized samples in memory 355. The digitized data can also be used to produce processed data, such as by filtering and/or digital signal processing (DSP). As an example, sampled signals obtained from an accelerometer can be filtered data or unfiltered data (sometimes referred to as "raw" data). In yet another embodiment, the processing includes functions useful to calculate minute ventilation (MV), or minute volume, from sensed signals. Examples of functions useful in calculating MV can be found in U.S. Pat. No. 6,076,015, "Rate Adaptive Cardiac Rhythm Management Device Using Transthoracic Impedance," Hartley et al., which is assigned to Cardiac Pacemakers, Inc., and which is incorporated herein by reference in its entirety, including its techniques for calculating MV.

The controller circuit 350 also analyzes the sampled or processed data to detect events associated with the heart activity. Some examples of these activity related events include sensed intrinsic activity or paced activity associated with a right or left atrium, sensed intrinsic activity or paced activity associated with a right or left ventricle, and the like. When the controller circuit 350 detects an event it stores a corresponding event marker in memory 355. The event marker is typically encoded as a numeric value. The IMD 300 includes a clock circuit 360. The clock circuit 360 provides a readable value that represents the passing of time. The controller 350 reads values that represent absolute time from the clock circuit 360. When the controller circuit 350 stores an event marker in memory 355, the marker is stored along with a timestamp that represents absolute time in a marker buffer 365.

Absolute time refers to the controller reading and storing a clock circuit value. This is in contrast to a controller calculating a relative time value between the present event marker and a previously sent data value, a previous cardiac event, or other implanted device related event. In one embodiment, the IMD 105 stores data for later retrieval by an external device, and absolute time is referenced from a system epoch, such as the beginning of the year 2000, for example. In one example of such an embodiment, the absolute time value is stored as forty-eight bits of data. In another embodiment, such as where the IMD 105 transmits data in real time to an external device, absolute time is referenced within a smaller window of time, so that it can be represented by less bits. In one example of such an embodiment, the absolute time is stored as a sixteen-bit value. In another embodiment, the clock circuit 360 includes a counter that rolls over every few minutes and absolute time is referenced within a window of a few minutes. In one example of such an embodiment, the counter rolls over every two minutes and absolute time is referenced within a two-minute window.

Figure 4:
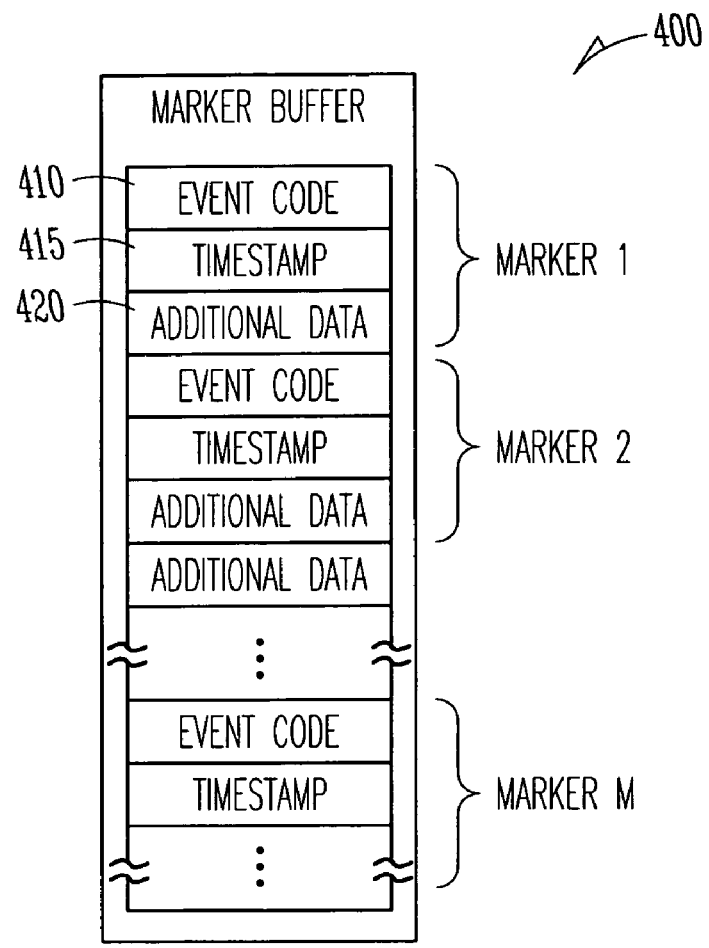
FIG. 4 shows one embodiment of a data structure to store markers in a buffer.

In one embodiment, the markers are stored in marker buffer 365 as a data structure. FIG. 4 shows one embodiment of a data structure 400 to store markers in marker buffer 365. The marker data structure 400 holds a variable number of markers. This is shown as Markers 1 through M in the figure, where M is an integer. Each marker includes a detected event code 410 to identify the type of marker and a timestamp 415 to identify when the marker occurred. As discussed above, the timestamp represents absolute time. Depending on the type of marker, zero to four bytes of additional data 420 are stored with the marker.

Returning to FIG. 3, the controller circuit 350 stores the sampled data into memory 355, either for buffering for real-time telemetry, or for a longer storage period before the data is transmitted by the telemetry. The sources of the sampled data, such as the leads and sensors, are sometimes referred to as data channels or sense channels. Each channel of the data is stored in a separate channel buffer 370. In one embodiment, the sampled data is stored in a channel buffer 370 as a data structure. In another embodiment, the controller circuit 350 creates one channel buffer 370 for each channel of sampled data, where each channel buffer 370 contains a data structure.

A discussion of a controller dynamically allocating memory into channel buffers 370 is found in co-pending Lent et al. U.S. patent application Ser. No. 10/680,731, entitled "METHOD AND APPARATUS FOR MANAGING DATA FROM MULTIPLE SENSING CHANNELS," which is assigned to Cardiac Pacemakers, inc., and which was filed on Oct. 7, 2003, and which is incorporated herein by reference in its entirety, including its discussion of using channel buffers.

In yet another embodiment, the controller circuit 350 executes a data compression algorithm on the sampled values and stores the sampled values as compressed data. In one example of this embodiment, the compression algorithm performs amplitude compression. Amplitude compression, in effect, compresses the voltage amplitude of the sampled electrical signal by reducing the resolution of the sampled data value, for example, from sixteen bits to eight bits. In another example of the embodiment, the controller circuit 350 compresses the data by reducing the rate at which the sampler circuit 340 collects data. In yet another example, the compression algorithm performs Huffman encoding to compress the sampled data.

Figure 5:
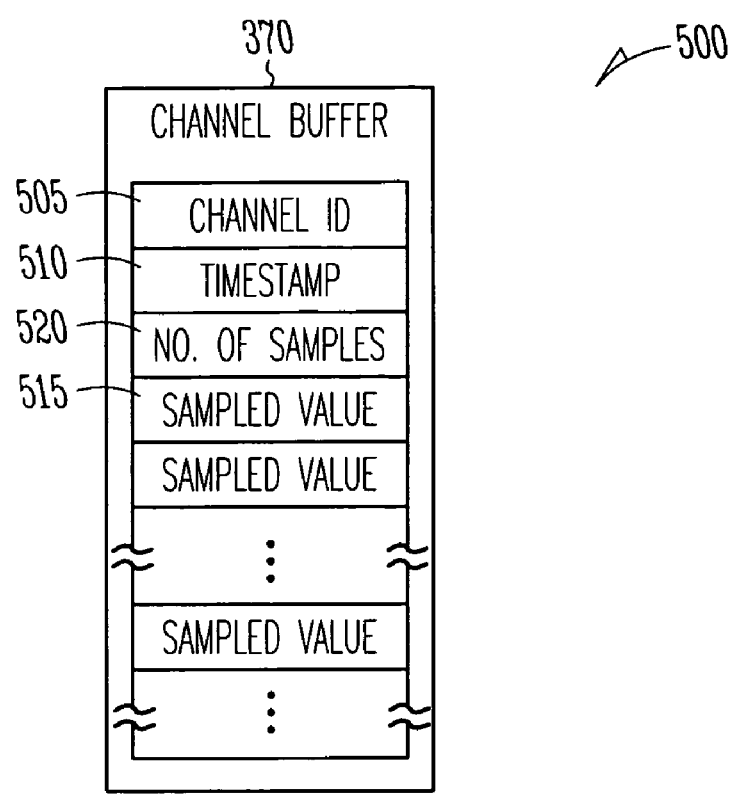
FIG. 5 shows one embodiment of a data structure to store sampled data in a channel buffer.

FIG. 3 shows N channel buffers 370 in memory 355, where "N" is an integer. FIG. 5 shows one embodiment of a data structure 500 to store sampled data in a channel buffer 370. In one embodiment, the data structure 500 includes a data channel identifier 505, timestamp 510 to identify (in absolute time) when sampling of data from the channel was begun, and a variable amount of sampled data 515. In another embodiment, the data structure 500 also includes the number of sampled data values 520 included in the data structure 500.

In FIG. 3, the IMD 300 also includes a telemetry circuit 375 to communicate with an external device 125. The telemetry circuit 375 is used to receive programming information from the external device 125 into memory 355. Data is received into the telemetry circuit 375 and moved into the telemetry receive buffer 380 before being moved to another location in memory 355. In this way, the external device 125 can change operational parameters in the IMD 300. Telemetry circuit 375 is also used to transmit data to the external device 125. To transmit data, controller circuit 350 reads data from memory 355, modifies the data for telemetric transmission, and writes it into the telemetry buffer 380. The controller circuit 350 then sends the data to the telemetry circuit 375 for transmission at a rate dictated by a predetermined telemetry communication protocol. The external device 125 is used to display the information for the caregiver.

In one example, the transmission of data from the IMD 300 is initiated by the external device 125. In one embodiment, the external device 125 is a programmer that can change the therapy provided by the IMD 300. In another embodiment, the external device 125 is a clinical device capable of storing data obtained from the IMD 300 in a database. In yet another embodiment, the database is a patient history database. In yet another embodiment, the external device 125 includes processing circuitry to determine and display trending in patient data received from the IMD 300. In yet another embodiment, the external device 125 is connected to a global computer network, such as the internet for example, or other communications network. In yet another embodiment, the external device 125 includes a communication module capable of transferring the data to a database accessed by a global computer network. In yet another embodiment, the external device 125 includes a wireless local area network (LAN) module and communicates with the IMD 300 using the wireless LAN.

Figure 6:
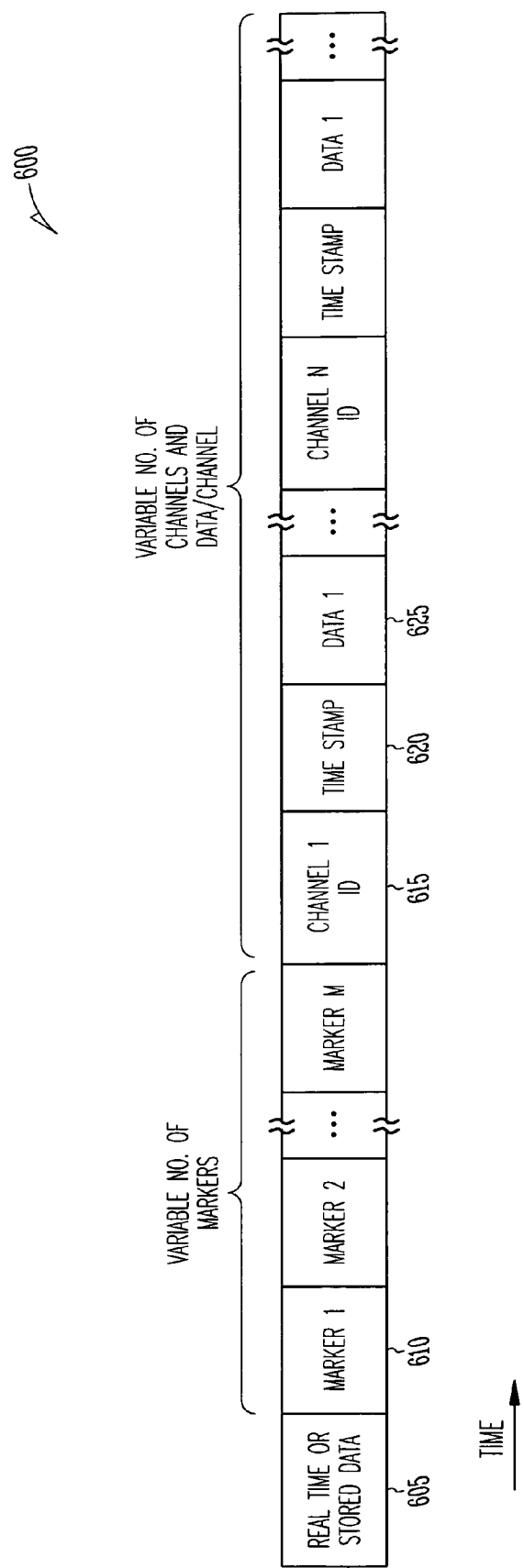
FIG. 6 shows an embodiment of a communication protocol used to transmit data from an implantable medical device to an external device.

FIG. 6 shows an exemplary embodiment of a communication protocol 600 used to transmit data from the IMD 300 to the external device 125. A communication protocol includes a predefined order of data communicated between two or more devices. The protocol provides, among other things, that data is to be transmitted within predefined time slots of the transmission session. In the embodiment in FIG. 6, the first bit of data (b0) is on the left and transmission of subsequent data proceeds to the right.

The protocol illustrated in FIG. 6 begins by sending an indication 605, during the first time slot, of whether the data that follows is being sampled and transmitted in substantially real time or was sampled and stored substantially earlier. In one embodiment, this indication includes a bit to indicate that either real time or stored data follows. Such a bit may also be incorporated into a session start flag value that indicates the beginning of a telemetry transmission. In another embodiment, the indication includes a message header comprising a message identifier, an indication of the data length to follow, and any other attributes of the message. In yet another embodiment, the message header and data contents are further embedded within the transmission protocols.

Next, the protocol 600 then transmits the marker buffer 365. This is transmitted as a variable amount of markers 610 in a variable amount of time slots. In FIG. 6, "M" markers are sent from the marker buffer 365, where "M" is an integer. In one embodiment, the markers include event codes and timestamps. In another embodiment, the markers further include additional bytes of data; the amount of additional data depending on the type of marker. In one such example, four bytes of additional data are sent.

After the marker buffer is transmitted, the protocol 600 then continues with the transmission of a variable amount of sampled data values 625. In one embodiment, the data is sent as a data structure from a single channel buffer. In another embodiment, the data is sent from more than one channel buffers, such as a variable number of channel buffers. In FIG. 6, a variable amount of sampled data values are sent from "N" channel buffers where "N" is an integer. Thus, in this example, the number of time slots used to transmit the sampled data values varies with the amount of data values and the number of channel buffers. In one embodiment, the data includes a channel identifier 615, a timestamp 620, and a variable amount of sampled data values 625. In another embodiment, the data also includes the number of sampled data values for that channel.

The external device 125 receives data transmitted from the IMD 300 into a buffer. Typically, the external device 125 includes a processor. As the buffer is filled, the processor of the external device 125 reconstructs the information transmitted from the buffers in the IMD 300 for a display such as a screen display or strip chart recorder. The processor of the external device 125 uses the timestamp information to align the information to be displayed (e.g., event markers and sampled data), such as to a common display axis that represents time. In this way, the events are aligned with respect to each other and need not be aligned using the sampled data. If compressed data is sent by the IMD 300, the processor of the external device 125 also decompresses the data.

FIG. 7 is an illustration of one embodiment of a screen display 700 of an embodiment of an external device 125. The display 700 shows four traces 705, 710, 715, 720 corresponding to heart activity. The display 700 also shows detected heart activity events by displaying markers 725. Traces 710 and 715 are examples of surface electrocardiogram (ECG) traces, which is acquired by the external device 125 from external (surface) ECG electrodes attached to the patient's skin, rather than from the IMD 300. Traces 705 and 720 are internally-obtained ECG traces that are reconstructed from the information transmitted from an IMD 300. Trace 705 is a trace reconstructed from sampled signals sensed in an atrium of a patient's heart. Trace 720 is a trace reconstructed from sampled signals sensed in a right ventricle of the patient's heart. Event markers 725 indicate heart activity events. Displaying event markers 725 assists a caregiver in diagnosing the heart activity. The markers 725 shown in FIG. 7 include an atrial sensed event (AS), a right ventricle sensed event (RVS), and a left ventricle sensed event (LVS). The external device 125 uses the timestamp information provided by the IMD 300 to align the markers 725 on the display 700 to the atrial trace 715 and the ventricular trace 720 on the display 700.

When data is sent from the IMD 300 in substantially real time, the IMD 300 buffers enough sampled data values and markers for efficient transmission while reducing or minimizing latency in the system. This system latency includes latency due to buffering, processing and transmission. In one embodiment, the IMD 300 buffers the sampled data values and markers using a one hundred millisecond (100 ms) buffer time interval. The gap in the traces shown in FIG. 7 designate where the screen is being refreshed; it is not indicative of a gap in the data. If a gap in the data does occur (due to communication interference, noise, misplacement of telemetry device 130, etc. . . . ) the external device 125 fills in the gap with a baseline value. Unlike such substantially real-time transmission, when previously stored data is sent from the IMD 300, the IMD 300 buffers the sampled data values and markers using a buffer time interval of seconds or even minutes.

Although specific examples have been illustrated and described herein, it will be appreciated by those of ordinary skill in the art that any arrangement calculated to achieve the same purpose could be substituted for the specific example shown. This application is intended to cover any adaptations or variations of the present invention. Therefore, it is intended that this invention be limited only by the claims and their legal equivalents.

What is claimed is:

1. A system comprising:
an implantable medical device, the implantable medical device comprising:
at least one electrical input, to receive sensed electrical activity of a heart;
a sampler circuit, coupled to the at least one electrical input, operable to generate sampled values of the sensed electrical activity;
a clock circuit, the clock circuit operable to generate readable values, wherein the clock circuit and the readable values roll over every few minutes;
a memory, including an event marker buffer; and
a controller circuit, coupled to the sampler circuit, the clock circuit, and the memory, the controller circuit operable to:
process the sampled values to generate at least one marker to indicate a detected event related to the sensed electrical activity,
read a clock circuit value as a timestamp denoting when the detected event occurred referenced with respect to a clock circuit time window of a clock circuit that rolls over every few minutes; and
store the at least one marker with the timestamp in the event marker buffer of the memory; and
an external device operable to receive information, including the marker with the timestamp, in substantially real time from the implantable medical device and to use the timestamp to align the information on a display.

2. The system of claim 1, wherein the controller circuit generates a plurality of markers, and wherein each event marker is stored in the event marker buffer as a data structure, the data structure comprising a variable number of event marker entries, wherein the entries include:

an event marker code;

the timestamp of when the event occurred; and additional data, if indicated by the event marker code, wherein the type and amount of additional data is defined by the event marker code.

3. The system of claim 1, wherein the system further includes an external device to communicate with the implantable medical device, and wherein the implantable medical device further includes a telemetry circuit to transmit the at least one event marker to the external device together with an indication of whether the information is transmitted in substantially real time or was sampled and stored substantially earlier.

4. The system of claim 3, wherein the at least one electrical input includes a plurality of electrical inputs coupled to the sampler circuit, each input corresponding to a signal channel, and wherein the memory includes at least one channel buffer to store sampled values, sampled values are stored in the at least one channel buffer as a data structure, the data structure having entries, the entries including:

a signal channel identifier;

the timestamp of when sampling of an electrical input began; and a variable number of sampled values.

5. The system of claim 4, wherein the telemetry circuit transmits the sampled values and event markers in a plurality of time slots, including a first set of time slots to transmit a variable amount of event markers from the event marker buffer and a second set of time slots to transmit a variable amount of sampled values from a variable number of channel buffers.

6. The system of claim 4, wherein the electrical inputs are coupled to a plurality of electrodes, the electrodes placed at different locations of a heart to sense electrical activity of a heart.

7. The system of claim 6, wherein at least one electrical input is coupled to a sensor, wherein the sensor generates electrical signals related to a physiologic parameter of a patient.

8. The system of claim 3, wherein the external device includes:

a buffer to receive the sampled values, markers and timestamps;

a processor operable to reconstruct a representation of the signals sensed on the electrodes and of the activity events using the timestamps; and a display operable to display the reconstructed representation of the signals.

9. The system of claim 8, wherein the implantable device is operable to transmit the sampled values and the detected event markers as they are accumulated in substantially real time, and wherein an amount of sampled values and markers are stored in the memory buffers.

10. The system of claim 9, wherein the amount of sampled values and markers are stored in the memory buffers memory buffers store is an amount that occurred during about a one hundred milliseconds (100 ms) buffer time window.

11. The system of claim 8, wherein the controller stores the sampled values generated from the channels in association with a timestamp as compressed data, and wherein the processor of the external device is operable to decompress the data.

12. The system of claim 11, wherein the controller is operable to perform amplitude compression to compress the data.

13. The system of claim 11, wherein the controller is operable to reduce the sampling rate to compress the data.

14. The system of claim 11, wherein the controller is operable to perform Huffman encoding to compress the data.

15. The system of claim 3, wherein the external device is operable to communicate with a global computer network.

16. The system of claim 1, wherein the implantable medical device includes an implantable cardioverter defibrillator.

17. The system of claim 1, wherein the implantable medical device is a cardiac rhythm management device.

18. A method comprising:

sensing electrical activity of a heart using an implantable device;

detecting, using the implantable device, events associated with the electrical activity;

generating and storing event markers representing the events in a memory included within the implantable device, the generating of each event marker including generating a timestamp of when a corresponding event occurred, the timestamp denoting when the event occurred referenced with respect to a clock circuit time window generated by a clock circuit, in the implantable device, including using the clock circuit to generate a clock circuit time window that rolls over every few minutes;

transmitting the event markers, including respective timestamps, from the implantable device to an external device in substantially real time; and using the timestamp to align information on a substantially real time display of the external device.

19. The method of claim 18, wherein the sensing electrical activity includes:

sensing electrical activity at a plurality of locations of a heart;

converting the electrical activity into data suitable for storage in the memory; and storing the data in one or more buffers in the memory, including allocating a buffer for each location of the sensing, and including storing a timestamp in each buffer indicating when the electrical activity of the data was sensed, and wherein the method further includes transmitting the data and timestamps corresponding to the data to the external device.

20. The method of claim 19, wherein the transmitting the data and the transmitting the event markers to an external device includes transmitting data and event markers in a plurality of time slots, including a first set of a variable number of time slots to transmit a variable amount of event markers and corresponding timestamps, and a second set of a variable number of time slots to transmit a variable amount of the data and corresponding timestamps.

21. The method of claim 20, wherein the transmitting the data and the transmitting the event markers includes transmitting an identifier to identify a sensing location associated with the data.

22. The method of claim 20, wherein transmitting the data, timestamps and event markers to an external device includes:

buffering the data in the external device;

aligning the data and the event markers in accordance with time using the timestamps; and displaying the data from the plurality of locations and the event markers according to their timing relationship with respect to the time.

23. The method of claim 22, wherein displaying the data includes displaying a baseline value when the data contains gaps because a communication link is lost.

24. The method of claim 19, wherein converting the electrical activity into data includes converting the electrical activity into compressed data using a compression algorithm.

25. The method of claim 19, wherein converting the electrical activity into compressed data using a compression algorithm includes using amplitude compression.

26. The method of claim 19, wherein converting the electrical activity into compressed data using a compression algorithm includes using Huffman encoding.

27. The method of claim 19, wherein converting the electrical activity into compressed data using a compression algorithm includes reducing the sampling rate to compress the data.

28. The method of claim 18, wherein sensing the electrical activity and converting the sensed activity into data includes sensing and converting in substantially real time, and wherein storing in memory includes buffering data and event markers for transmission to an external device in substantially real time.

29. The method of claim 28, wherein the timestamp includes an indication of time measured within a two-minute window.

30. The method of claim 18, wherein storing in memory includes storing data and event markers for later retrieval by the external device.

31. The method of claim 30, wherein the timestamp includes an indication of time measured from a system epoch.

32. The system of claim 1, wherein the timestamp is referenced within a time window of approximately two minutes.

* * * * *

UNITED STATES PATENT AND TRADEMARK OFFICE
CERTIFICATE OF CORRECTION

PATENT NO. : 7,471,980 B2
APPLICATION NO. : 10/743567
DATED : December 30, 2008
INVENTOR(S) : Koshiol et al.

It is certified that error appears in the above-identified patent and that said Letters Patent is hereby corrected as shown below:

In column 9, lines 55-58, delete "10. The system of claim 9, wherein the amount of sampled values and markers are stored in the memory buffers memory buffers store is an amount that occurred during about a one hundred milliseconds (100 ms) buffer time window." and insert -- 10. The system of claim 9, wherein the amount of sampled values and markers that are stored in the memory buffer is an amount that occurred during about a one hundred milliseconds (100 ms) buffer time window. --, therefor.

Signed and Sealed this

Twenty-sixth Day of January, 2010

David J. Kappos
*Director of the United States Patent and Trademark Office*